United States Patent [19]

Lipscombe et al.

[11] Patent Number: 5,589,384

[45] Date of Patent: Dec. 31, 1996

[54] FUSION PROTEINS

[75] Inventors: Martin J. Lipscombe, Cambridge; Ian G. Charles; Neil F. Fairweather, both of Beckenham, all of United Kingdom

[73] Assignee: Glaxo Wellcome Inc., Research Triangle Park, N.C.

[21] Appl. No.: 237,716

[22] Filed: May 2, 1994

Related U.S. Application Data

[63] Continuation of Ser. No. 896,003, Jun. 11, 1992, abandoned.

[30] Foreign Application Priority Data

Jun. 11, 1991 [GB] United Kingdom ............... 9112553.4

[51] Int. Cl.$^6$ ............................ C12N 15/61; C12N 1/00; C12N 1/21; C12N 15/63; C07K 14/28; C07K 14/24

[52] U.S. Cl. ................................ 435/252.33; 435/252.3; 435/320.1; 435/69.3; 435/172.3; 435/69.7; 435/240.1; 435/254.11; 536/23.4; 530/350; 530/802; 530/808

[58] Field of Search .................. 536/23.4; 435/69.7, 435/69.3, 320.1, 240.1, 252.3, 252.33, 254.11

[56] References Cited

U.S. PATENT DOCUMENTS 4,898,818  2/1990  Nakai et al. .......................... 435/69.1

FOREIGN PATENT DOCUMENTS

WO86/06635  11/1986  WIPO.
WO90/06366  6/1990  WIPO.

OTHER PUBLICATIONS

Lipscombe (1991) "Construction and characterisation of *Escherichia coli* heat labile toxin B–subunit fusion proteins (enterotoxin)" Ph.D. Dissertation, U. Warwick, U.K.

Nashar et al, "Current progress in the development of the B subunits of cholera toxin and Eschericihi coli heat–labile enterotoxin as carriers for the oral delivery of heterologous antigens and epitopes", Vaccine 11:235–240 (1993).

Hirst, "Assembly and Secretion of Oligomeric Toxins by Gram–Negative Bacteria", Sourcebook of Bacterial Protein Toxins, Chapter 5, pp. 75–100 (1991) London: Academic Press.

Fergusson et al, "A Multivalent Carrier for Delivery of Epitopes and Anitgens Based upon the B–subunit Enterotoxoid of Eschericiha coli", Bacterial Protein Toxins, Zbl. Bakt. Suppl. 19, Rappuoli et al (Eds.), pp. 519–520 (1990).

Spangler, "Structure and Function of Cholera Toxin and the Related Escherichia coli Heat–Labile Enterotoxin", Microbiological Reviews 56(4):622–647 (1992).

Guzman–Verduzco et al J. Bacteriol 169, No. 11 5201–5208, Nov. 1987 "Fusion of Escherichia coli Heat–Stable . . . Subunit".

Purvis et al J. Mol. Biol. 193, 413–417, 1987 "The efficiency of Folding of Some Proteins is Increased . . . Translation in Vivo".

Sandkvist et al. J. Mol. Biol. 169, 4570–4576 1987 "Alterations at the Carboxyl Terminus . . . Enterotoxin".

Sanchez et al, Gene 64, 265–175, 1988 "Hybrid enterotoxin LTA:: STa proteins and their protection . . . enterotoxin".

Dertzbaugh et al, Gene 82, 335–343, 1989 "Plasmid Vectors for constructing translational fusions to the B . . . toxin".

Dertzbaugh et al, Infect. Immun. 58, 70–79, 1990 "Cholera Toxin B–subunit Gene Fusion: Structural and Functional . . . Chimeric Protein".

Schodel et al, Infect. Immun. 57, 1347–1350, 1989 "Construction of a Plasmid for Expression of Foreign Epitopes . . . Enterotoxin".

van Heyningen, Nature 351, 351, May 1991 "Enterotoxins The ring on a Finger".

Sixma, Nature 351, 371–377, May 1991 "Crystal structure of a cholera toxin–related . . . E. coli".

Lipscombe et al, Mol. Microbiol. 5, 6, 1385–1392, 1991 "Intranasal immunization using the B subunit . . . antigen".

Clements, Infect. Immun 58 1159–1166, 1990 "Construction of a Nontoxic Fusion Peptide for Immunization . . . Enterotoxins".

Daum et al, "Production of human adrenocorticotropin by cleavage of alkaline–phosphatase–derived fusion proteins containing repetitive recognition sequences for collagenases", Eur. J. Biochem. 185 3/7 (1989).

*Primary Examiner*—Robert A. Wax
*Assistant Examiner*—Gabriele E. Bugaisky
*Attorney, Agent, or Firm*—Nixon & Vanderhye P.C.

[57] ABSTRACT

A fusion protein suitable for use as a vaccine comprises an amino acid sequence having biological activity which is fused via an intervening hinge comprising from two to eight glycine-proline repeats to the C-terminus of sufficient of the amino acid sequence of a B subunit of an enterotoxin which is capable of ADP-ribosylation of a GTPase.

25 Claims, 5 Drawing Sheets

FUSION PROTEINS

This is a continuation of application Ser. No. 07/896,003, filed Jun. 11, 1992, now abandoned.

This invention relates to fusion proteins, their preparation and use.

Cholera toxin (CT) and the *Escherichia coli* heat labile toxin (LT) are very closely related proteins produced by *Vibrio cholerae* and enterotoxigenic *E. coli* strains respectively (Clements and Finkelstein, 1979). Like CT, LT consists of a 28 kDa A subunit (LTA) and a non-covalently associated heat-labile B subunit (LTB) comprising five identical 11.5 kDa monomers. The A-subunit is responsible for toxicity, possessing NAD-ribosylating activity which irreversibly activates the target cell adenylate cyclase complexes (Moss and Richardson, 1978). Entry of the toxic A subunit into the cell is facilitated by the non-toxic B-subunit. This B subunit comprises a 56 kDa pentamer which binds to $GM_1$, the monosialoganglioside toxin receptor (Cuatrecasas, 1973). $GM_1$ is present on the surface of a variety of mammalian tissues, including mucosal epithelium.

CT, and the non-toxic subunits CTB and LTB, are exceptionally potent mucosal immunogens when given orally or intranasally, a property believed to be due in part to the $GM_1$ binding properties of the B subunits (Pierce, 1978). This is in contrast to most proteins which are poorly immunogenic when administered orally, requiring large amounts of antigen to elicit, at best, a modest secretory immune response. CT also induces a systemic response and does not induce oral tolerance which is a common feature of soluble proteins administered by this route (see De Aizpurua and Russell-Jones, 1988).

CTB and LTB have attracted much attention as potential vaccines, particularly as adjuvants for the targeted delivery of foreign antigens. CTB has been shown to enhance the immune response to chemically coupled antigens when given either orally (Czerkinsky et al, 1989; Liang et al, 1988) or intranasally (Bessen and Fischetti, 1988; Tamura et al., 1988). Of particular interest is the stimulation of mucosal immunity against a chemically coupled protein or a co-administered protein when given intranasally (McKenzie and Halsey, 1984; Tamura et al, 1988).

Genetic fusion of antigens to carrier proteins such as LTB offers many advantages over chemical coupling. Antigens or short peptide fragments defining epitopes of any desired sequence can be fused to the carboxy or amino termini of the carrier. The fusion proteins thus have a defined composition which is consistent from batch to batch and is easily analysed. There have been several reports of gene fusions of LTB or CTB to foreign antigens (Guzman-Verduzco and Kupersztoch, 1987; Sanchez et al, 1988; Schodel and Will, 1989; Dertzbaugh and Macrina, 1989; WO 86/06635; WO 90/06366). While in some cases the structure and properties of the chimeric proteins were shown to be similar to the native carrier (Dertzbaugh et al, 1990), other alterations or additions to the LTB carrier destroyed some or all of the properties of the native molecule (Clements, 1990; Sandkvist et al, 1987). Schodel and Will (1989) were unable to detect antiviral antibodies in mice fed with attenuated *Salmonella dublin* expressing hepatitis B virus sequences fused to LTB.

According to the present invention, there is provided a fusion protein which comprises an amino acid sequence having biological activity which is fused via an intervening hinge comprising from two to eight glycine-proline repeats to the C-terminus of sufficient of the amino acid sequence of a B subunit of an enterotoxin which is capable of ADP-ribosylation of a GTPase.

The fusion proteins fold correctly and assemble into stable pentamer complexes. The fusion proteins are capable of binding to $GM_1$-gangliosides whilst presenting the amino acid sequence having biological activity. A fusion protein which presents heterologous epitope can therefore be used as a vaccine. A fusion protein which presents an amino acid sequence having pharmaceutical activity can be used as a means of delivering the pharmaceutically active sequence to a patient.

A fusion protein comprises sufficient of the amino acid sequence of a B subunit of an enterotoxin which is capable of ADP-ribosylation of a GTPase such that the fusion protein is capable of forming oligomers which bind to $GM_1$ ganglioside. This part of the fusion protein may be termed the B subunit moiety. Substantially all of a B subunit of such an enterotoxin may therefore be present. A fusion protein may comprise LTB or CTB. The amino acid sequence of a natural B subunit such as LTB or CTB may in fact be modified by one or more amino acid substitution, insertion or deletion. Antibody raised against the natural B subunit may bind to a fusion protein comprising a modified version of the amino acid sequence of that subunit.

Such a modified amino acid sequence may be employed provided the fusion protein incorporating the modified sequence retains an ability to form pentamers and to bind to $GM_1$-ganglioside. The physicochemical character of the original sequence should be preserved, i.e. in terms of charge density, hydrophobicity/hydrophilicity, size and configuration. Candidate substitutions are, based on the one-letter code (Eur. J. Biochem. 138, 9–37, 1984):

A for G and vice versa;
V by A, L or G;
K by R;
S by T and vice versa;
E by D and vice versa; and
Q by N and vice versa.

There may be a degree of homology of 80% or more, for example 90% or more or 95% or more, between the natural sequence of an enterotoxin B subunit and a modified amino acid sequence. The natural amino acid sequence of a B subunit may be shortened, for example by up to 4 or up to 2 amino acid residues, at either or each terminus. The C-terminus of LTB or CTB may be shortened in this way, therefore.

A hinge is provided in a fusion protein of the invention between the B subunit moiety and the heterologous epitope or pharmaceutically active agent. The hinge comprises from two to eight repeats of the amino acid sequence Gly-Pro. There may be up to four repeats, for example. The hinge is fused to the C-terminus of the B subunit moiety.

The Gly-Pro repeat sequence may be flanked by other amino acid residues. These are suitably uncharged non-aromatic residues. Up to four amino acid residues, for example two amino acid residues or one amino acid residue, may be provided after the B subunit moiety and before the Gly-Pro repeat sequence. Up to four amino acid residues, for example two amino acid residues or one amino acid residue, may be provided after the Gly-Pro repeat sequence and before the heterologous epitope or pharmaceutically active agent.

Any amino acid sequence having biological activity may be attached to the C-terminus of the hinge. The length of the sequence is not of critical importance. The sequence should not, though, disrupt the ability of the fusion protein to form oligomers which bind to $GM_1$-ganglioside. The sequence may be up to 200, up to 150 or up to 100 residues long. A shorter sequence of up to 60, for example up to 30 or 20, amino acid residues in length may be employed.

Any amino acid sequence comprising an antigen or epitope from a pathogen responsible for a human or veterinary disease may be presented by the fusion protein. The antigen or epitope may be one which is capable of effecting an immune response, e.g. raising neutralising or non-neutralising antibodies or cellular immunity. A predicted antigenic determinant may be employed.

A foreign amino acid sequence is therefore fused to the B subunit moiety. This may therefore comprise an antigenic determinant capable of raising neutralising antibody to a pathogenic organism. The pathogen may be a respiratory- or gut-associated pathogen. The epitope may be derived from a virus, bacterium, fungus, yeast or parasite. More especially, the epitope may be derived from a type of human immunodeficiency virus (HIV) such as HIV-1 or HIV-2, hepatitis A or B virus, human rhinovirus such as type 2 or type 14, herpes simplex virus, poliovirus type 2 or 3, foot-and-mouth disease virus, influenza virus, coxsackie virus, the cell surface antigen CD4, *Chlamydia trachomatis*, *Bordetella pertussis*, and the heat-stable enterotoxin of *E. coli* (ST).

LTB may therefore be fused to an immunogenic portion of ST. The LTB can be fused to the core and toxin regions of ST or to the toxin region only. For example, LTB can be linked to a portion of ST beginning at ST amino acid number 19 (Pro) or at ST amino acid number 49 (Gly). Both the long and short hybrid proteins which result include the entire nineteen carboxy-terminal amino acid residues of ST which contain the six Cys residues necessary for native ST configuration.

A pharmaceutically active peptide may be fused to the C-terminus of the hinge. An example of a pharmaceutically active peptide that could be coupled genetically to the hinge constructs is fragment 163–171 of human interleukin 1B (VQGEESNDK (SEQ ID NO:1) in the single letter code), which has immunostimulatory, immunorestorative, antitumoral and radio protective capacities comparable with those properties exhibited by the entire interleukin IL-1B protein. Other examples are cytokines and fragments of cytokines.

Another example of a biologically active peptide that could be coupled to the hinge is KTGSGFFVF (SEQ ID NO:2), found in the CH4 domain of human IgE. A response to this peptide has been described as being important in reducing IgE antibody formation and serum histamine levels, leading to a reduced allergic response.

A useful fusion protein may therefore be represented by the formula (I):

$$X-Y_1-(Gly\text{-}Pro)_n-Y_2-Z \qquad (I)$$

in which X represents the B subunit moiety, $Y_1$ and $Y_2$ are each independently peptide bonds or amino acid sequences of up to 4 amino acid residues, Z represents the amino acid sequence having biological activity and n is 2, 3 or 4. Preferably $Y_1$ is a leucine (L) residue and $Y_2$ denotes the amino acid residues glutamic acid-isoleucine (EI).

The fusion proteins are prepared by recombinant DNA methodology. More particularly, a fusion protein is prepared by a process which comprises maintaining a host, which has been transformed with a vector capable of expressing the fusion protein in that host, under such conditions that the fusion protein is expressed. The fusion protein can then be isolated, typically in biologically pure form.

The preparation of the fusion protein therefore depends upon the provision of a DNA sequence encoding the fusion protein. The DNA sequence may be provided at its 5'-end with a sequence encoding a leader for the fusion protein so that the fusion protein is exported from the cytoplasm of the host cell in which it is expressed. Any appropriate leader sequence may be employed. Typically, however, DNA encoding the natural leader sequence for the B subunit moiety is provided immediately upstream of the DNA encoding the amino acid sequence of the mature B subunit moiety.

The choice of codons specifying the residues of the hinge may be important. Suitably, at least half of the codons are rare codons for amino acid residues in the host in which a fusion protein is to be expressed. The codons should not therefore be the optimal codons, i.e. the codons of first choice, for use in the host. They generally should not be the codons of second choice. At least 75%, at least 90% or all of the codons for the hinge may be rare codons. For *E. coli*, such codons are reported by Sharp and Li (1986). Rare codons are thought to create pauses during translation which allow for the correct folding of the B subunit moiety independently of the hinge and hinge fusion.

Thus a DNA sequence encoding the desired fusion protein is provided. An expression vector is prepared which incorporates the DNA sequence and which is capable of expressing the fusion protein when provided in a suitable host. Appropriate transcriptional and translational control elements are provided for the DNA sequence, in particular a promoter for the DNA sequence and a transcriptional termination site. The DNA sequence is located between translation start and stop signals in the vector. The DNA sequence is provided in the correct frame such as to enable expression of the fusion protein to occur in a host compatible with the vector.

A preferred vector for use in the invention encodes the B subunit moiety and the hinge. The coding sequence for the hinge is selected so that it ends with a restriction site into which a gene can be inserted which encodes the amino acid sequence having biological activity. The restriction site allows the gene to be inserted in the correct reading frame.

Where the B subunit moiety is LTB, a vector capable of expressing LTB can first be obtained by cloning the LTB gene (Dallas, 1983) into a vector under the control of appropriate transcriptional and translational regulatory elements. Oligonucleotide(s) corresponding to the hinge can be synthesised and fitted to the 3'-end of the LTB gene. In particular, a DNA sequence encoding the hinge may be cloned into the SpeI site located at the natural termination codon of the 3'-end of the LTB gene. A gene encoding the amino acid sequence having biological activity can be cloned in phase into an appropriately located restriction site at the 3'-end of the DNA sequence encoding the hinge.

The expression vector which encodes the fusion protein is used to transform a host. Cells harbouring the expression vector are cultured so as to enable expression of the fusion protein to occur. The fusion protein may self-assemble into pentamers. Any appropriate host-vector system may be employed. The host may be a procaryotic or eucaryotic host. The vector may be plasmid. In that event, a bacterial or yeast host may be used, for example a Gram negative bacillus such as *E. coli* or a *Vibrio* species, or *S. cerevisiae*. Alternatively, the vector may be a viral vector. This may be used to transfect cells of a mammalian cell line, such as Chinese Hamster Ovary (CHO) cells or COS cells, in order to cause expression.

The fusion protein that is expressed can be isolated. Where a fusion protein is expressed with a leader sequence, the protein will have been exported from the cytoplasm of the cell in which it is expressed. A fusion protein expressed with a natural LTB leader sequence, for example, can therefore be isolated and purified from the periplasm of *E. coli*.

The purified fusion protein, killed toxigenic strains of *E. coli* in which the fusion protein has been expressed and attenuated live vaccines capable of expressing the fusion protein can each be used as vaccines in the case where it is a heterologous epitope which is fused via the hinge to the B subunit moiety. The vaccines typically also comprise a physiologically acceptable carrier or diluent. Conventional formulations, carriers and diluents may be employed. A suitable attenuated live vaccine may be an attenuated microorganism having a non-reverting mutation in each of two discrete genes in its aromatic biosynthetic pathway. Such microorganisms are described in EP-A-0322237. The microorganism is typically a pathogenic bacterium, for example from the genus *Salmonella* such as *S. typhi*, *S. typhimurium*, *S. dublin* or *S. cholerasius*.

The non-reverting mutations may occur in any of, typically in two of, the aroA, aroC, aroD and aroE genes. Preferably one of the non-reverting mutations is in the arOA gene. A suitable attenuated microorganism may harbour an expression cassette encoding a fusion protein such that the fusion protein can be expressed by the microorganism. For reliable expression through generations of the microorganism, an expression cassette should be stably inherited in the absence of antibiotic selection.

A vaccine may be administered by any convenient route. The choice of whether an oral route, an intranasal route or a parenteral route, such as subcutaneous, intravenous or intramuscular administration, is adopted, of the dose and of the frequency of vaccination depends upon the purpose of the vaccination, whether a human or animal is being treated and the condition of the human or animal to which the vaccine is to be given.

Typically, however, the fusion protein is administered in an amount of from 1–1000 μg per dose, more preferably from 10–100 μg per dose, by the oral, intranasal or parenteral route. For attenuated *S. typhi*, on the other hand, a dosage of $10^9$ to $10^{11}$ *S. typhi* organisms per dose is generally convenient for a 70 kg adult human patient, typically via the oral route.

In the case where a pharmaceutically active polypeptide is fused to the B subunit moiety, the fusion protein may be used to deliver the polypeptide to a patient. The fusion protein may be administered orally, intranasally or parenterally. The dosage depends on a number of factors including the purpose of the administration, the agent and the condition of the patient. Typically, however, the fusion protein is administered in an amount of from 1 to 1000 μg per dose, preferably from 10 to 100 μg per dose, by the oral, intranasal or parenteral route. The fusion protein can be formulated for administration as a pharmaceutical composition also comprising a pharmaceutically acceptable carrier or diluent. Any conventional carrier or diluent may be utilised.

The following Example illustrates the invention.

BRIEF DESCRIPTION OF THE DRAWINGS

FIG. 1 shows the construction of pFV1 and pFV169 plasmids. (A), Plasmid pBRD026 was cleaved with SpeI and the oligonucleotides of SEQ ID NOS: 3 and 4 inserted to form pFV1 (B). (C), DNA sequences (SEQ ID NOS: 8 and 10) and the amino acid sequence (SEQ ID NO: 9) encoded by the 5' end of pFV1. The region comprising the hinge is underlined. pFV1 was cut with BglII and SpeI and a pair of oligos inserted which encode the epitope recognised by the BB05 monoclonal antibody to form pFV169 (D) which expresses the LTB69 protein. (E), Amino acid sequence (SEQ ID NO:11) at the carboxy terminus of the LTB69 protein.

FIG. 2 shows the results of SDS-PAGE analysis of periplasmic fractions of *E. coli*. Lane 1, HB101 (unboiled); Lane 2, HB101 (boiled); Lane 3, HB101 pMMB68 (unboiled); Lane 4, HB101 pMMB68 (boiled); Lane 5, HB101 pFV1 (unboiled); Lane 6, HB101 pFV1 (boiled); Lane 7, HB101 pFV169 (unboiled); Lane 8, HB101 pFV169 (boiled). The LTB and LTB69 specific bands are labelled with an arrow.

FIG. 3B plates probed with BB05 monoclonal antibody.

FIG. 4 shows the results of SDS-PAGE analysis of purified LTB69 protein. Lane 1, total periplasmic proteins from HB101 (pFV169) (after concentration); lane 2, flow through from DEAE trisacryl column; lane 3, eluate from DEAE trisacryl column; lane 4, eluate from DEAE trisacryl column (boiled). All samples except lane 4 were applied unboiled. The LTB69 protein is arrowed. Molecular weight markers (kDa) are shown on the left.

EXAMPLE

MATERIALS AND METHODS

Bacterial strains, plasmids and oligonucleotides.

*E. coli* strain HB101 was used for the preparation of all plasmids. Bacteria were grown in Luria broth (LB) or LB solidified with 1.6% (wt/vol) agar (Davis et al., 1980). Plasmid pBRD026 (Maskell et al., 1987) is a 5.2 kb vector directing the constitutive expression of porcine LT-B from the P1 anti-tet promoter of pBR322. For the construction of pFV1, the following oligonucleotides were used: 5'CTTGGGGCCGGGGCCCGAGATCTTTGA (SEQ ID NO:3), and 5'CTAGTCAAAGATCTCGGGCCCCGGCCC (SEQ ID NO:4). These oligonucleotides were phosphorylated, annealed and cloned into the SpeI site of pBRD026 to form pFV1. Similarly the oligonucleotides 5'GATCGCTC-CGCAGCCGGGTCCGCAGCCGCCGCAGC-CGCCGCAGCCGCAGCCGGAGGC GCCGGCTCCG-CAGCCGGA (SEQ ID NO:5) and 5'CTAGTCCGGCTGCGGAGCCGGCGCCTC-CGGCTGCGGCTGCGGCGGCTGCGGCGGCTG CGGACCCGGCTGCGGAGC (SEQ ID NO:6) were cloned into the BglII and SpeI sites of pFV1 to form pFV169. DNA manipulations were carried out as described by Sambrook et al., (1989). The determination of DNA sequences of plasmid constructs was carried out by subcloning relevant fragments into M13mp18 and mp19 (Messing and Vieira, 1982). DNA sequencing was carried out using T7 polymerase (Tabor and Richardson, 1987) and synthetic oligonucleotide primers (Charles et al., 1986).

Enzyme linked immunoassays (ELISAs)

The $GM_1$-binding properties of LTB and its derivatives were analysed by a $GM_1$ ELISA technique described previously (Svennerholm & Holmgren, 1978). Purified LTB used as a standard was a kind gift from T. Mirst. Serum antibodies to LTB and P.69 were detected using routine ELISA procedures. The titre giving 50% maximum absorbance at 450 nm was determined, by plotting $A_{450}$ against $log_{10}$ serum dilution, and expressed as $log_{10}$ reciprocal of serum dilution.

Preparation and analysis of periplasmic extracts.

Periplasmic fractions of E. coli were prepared by the method of Hirst et al., (1984). Proteins were subsequently visualised by staining with Coomassie brilliant blue or electroblotted onto nitrocellulose and probed with polyclonal rabbit anti-LTB antisera, or with the P.69-specific mouse monoclonal antibody (mAb) BB05. Blots were further probed with anti-rabbit or anti-mouse immunoglobulin conjugated to horseradish peroxidase (Dakopatts, Copenhagen, Denmark) and developed with 4-chloro-1-naphthol (Sigma, Poole, U.K.). LTB and LTB fusion proteins were partially purified from E. coli periplasmic fractions as follows: overnight cultures were harvested and washed once in ice-cold phosphate-buffered saline (PBS). The cell pellet was then resuspended in ⅟25 of the original culture volume in 0.3 M sucrose buffered with 0.1 M phosphate to pH 7.6. Ethylene diamine tetra-acetic acid (EDTA) and lysozyme were added to a final concentration of 5 mM and 20 µg/ml respectively. The suspensions were left on ice for 20–25 minutes with occasional agitation and then centrifuged at 20,000×g for 15 minutes to pellet the spheroplasts. The supernatant was collected and concentrated by ultrafiltration using an Amicon Diaflo equipped with a XM50 membrane. The retentate was dialysed overnight at 4° C. against 50 mM NaCl buffered to pH8.6 with 25 mM Tris. The dialysed material was then loaded onto a DEAL Trisacryl column (Pharmacia, Sweden) equilibrated with the same buffer. After extensive washing the bound protein was eluted with a 50–250 mM NaCl gradient, buffered to pH8.6 as before. The $A_{280}$ nm of the eluate was continuously monitored with a UV-1 Single Path Monitor (Pharmacia, Milton Keyriss) and a Servoscribe 210 recorder (Camlab, Cambridge). Fractions were collected and analysed by dot-blotting onto nitrocellulose and probing with polyclonal antiserum specific for LTB. Positive fractions were further analysed by SDS-PAGE. Those with the highest purity of LTB or LTB69 were pooled. Total protein content was determined using the Pierce BCA assay.

Immunizations

6–8 week-old female BALB/c mice were lightly anaesthetised with ether and inoculated intra-nasally with 20 µg of LTB or LTB69 in a volume of 40 µl. After 4 weeks the animals were boosted with the same amount of antigen and by the same route. Samples of serum were taken prior to immunization and subsequently at 1–2 week intervals. Three weeks after boosting the mice were killed, lymphocytes isolated from lungs and antigen-specific ELISPOT assays were performed on lung homogenates (Jones et al., 1986) as described by Czerkinsky et al., (1983).

RESULTS

1. Construction of pFV1

In order to use the E. coli LTB as a carrier for foreign epitopes, we modified the plasmid pBRD026 which expresses LTB in E. coli under the control of the P1 promoter of pBR322 (Maskell et al, 1987). The SpeI site located at the termination codon at the 3' end of the gene was used to clone in an oligonucleotide specifying a sequence of amino acids encoding a "hinge" which would join the LTB protein in phase to the foreign epitope. The DNA sequence around this hinge region was also designed to include restriction sites for BglII and SpeI (see FIG. 1). The oligonucleotide sequence contains a base pair mismatch which does not allow the reformation of one of the SpeI sites and, when it is inserted in the correct orientation, also abolishes the stop codon at the end of the LTB gene. Hence the oligonucleotides are translated through to the stop codon at the reformed SpeI site. Oligonucleotides encoding epitopes can be cloned into the unique BglII and SpeI sites, and the epitopes will be expressed as fusions to the carboxy terminus of LTB.

Figure 1:
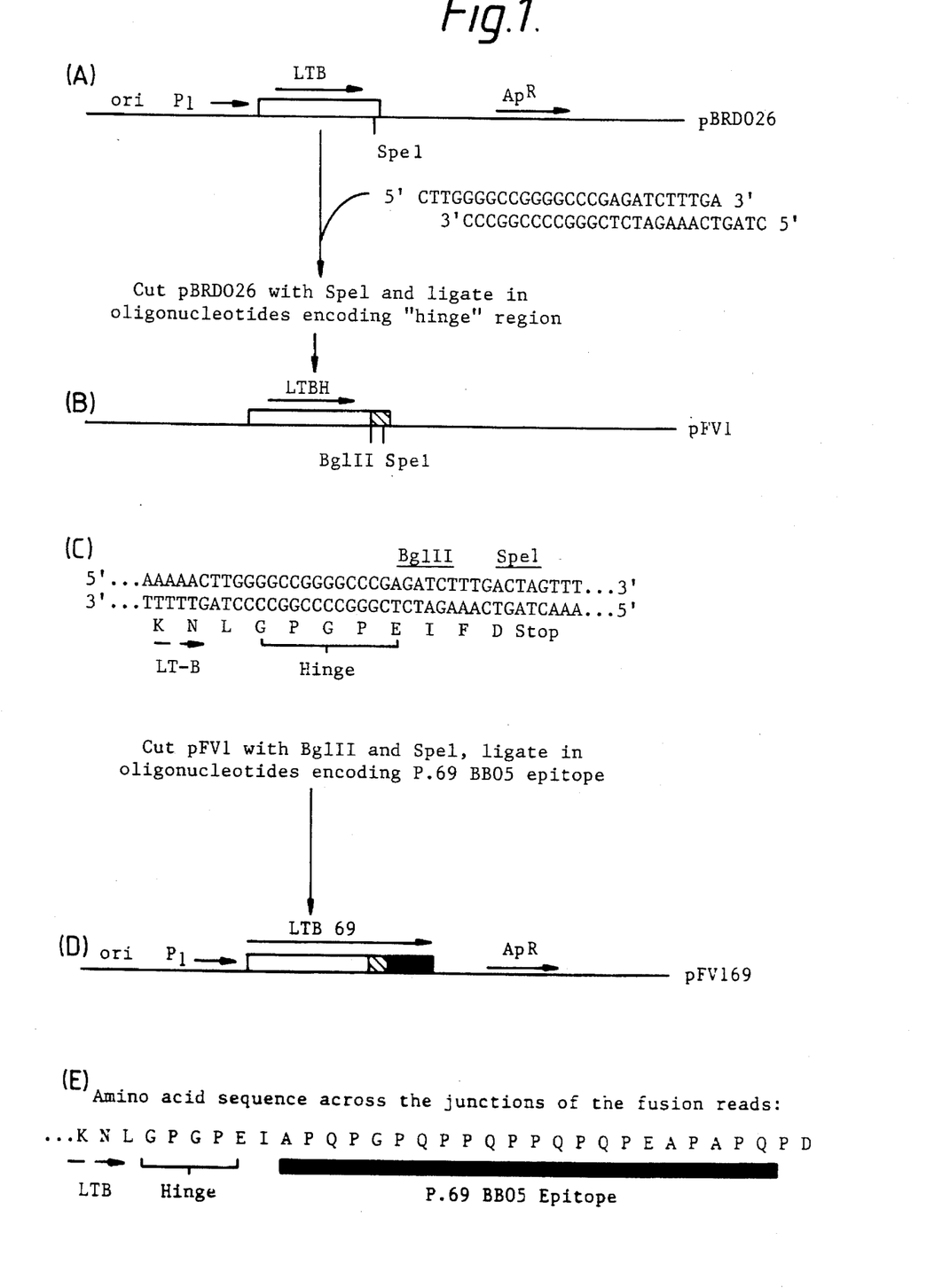

Insertion of the "hinge" oligonucleotide into plasmid pBRD026 resulted in the fusion plasmid pFV1 (see FIG. 1). pFV1 expresses full length LTB with an 8 amino acid glycine-proline extension (FIG. 1).

2. Construction of pFV169

To test the utility of pFV1 as a vector to construct stable fusions to LTB, we chose to link an epitope for a well defined monoclonal antibody to the carboxy terminus of LTB. The amino acid sequence Pro-Gly-Pro-Gln-Pro-Pro (SEQ ID NO:7) of the P.69 protein of B. pertussis has been identified as the epitope reactive with the protective monoclonal antibody BB05 (EP-A-0425082; Novotny et al., 1985). This well defined epitope was considered ideal for the insertion into pFV1. An oligonucleotide encoding this epitope was synthesised by BglII and SpeI ends (see FIG. 1), and was subsequently cloned directly into pFV1 digested with these enzymes. The DNA sequence across the junctions of the new construct, termed pFV169, was determined and found to be as predicted.

3. Characterisation of LTB fusion proteins by SDS-PAGE

Figure 2:
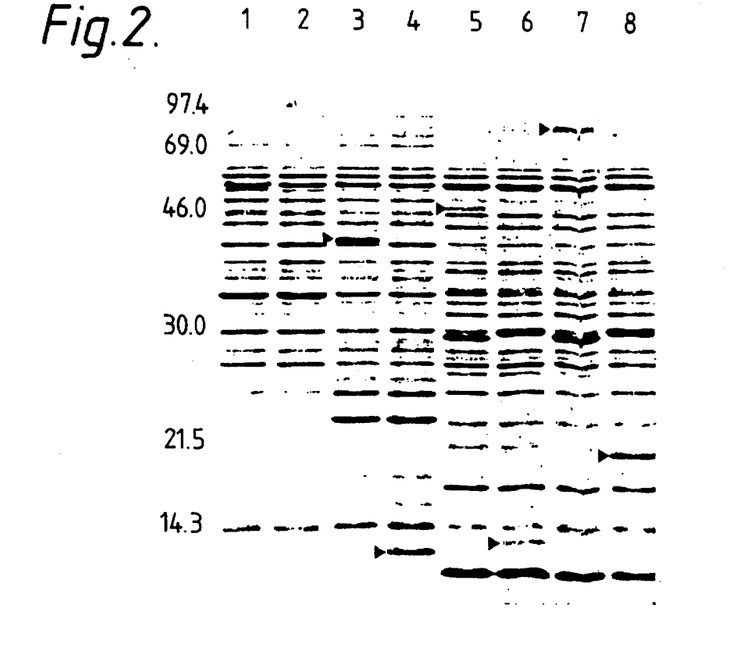

Alterations to the native LTB molecule produced by genetic manipulation can affect the properties of the molecule, including for example the ability to form pentamers, bind $GM_1$ gangliosides and associate with the A subunit of LT (Sandkvist et al., 1987). We therefore characterised the fusion proteins we had constructed in a number of ways. Cultures of E. coli containing pFV1 and pFV169 were grown in L-broth and periplasmic fractions prepared. SDS-PAGE analysis of these periplasmic fractions revealed that, like the native LTB subunit, LTBH and LTB69 were soluble and were transported to the periplasmic space (see FIG. 2). In addition, both proteins exhibited the characteristic behaviour of LTB, migrating as a monomer if boiled prior to SDS-PAGE or as a pentamer if loaded onto a gel without heat-treatment. As expected, the LTB69 fusion showed a considerable increase in molecular weight compared to LTB. The calculated molecular weight of the monomer of this fusion protein is 14 kDa, which is lower than the observed molecular weight of around 18 kDa (FIG. 2, lane 7). The LTB "hinge" monomer (LTBH), expressed by pFV1, also demonstrated a rather higher molecular weight than LTB alone. The increased molecular weight of the fusion proteins is even more apparent when unboiled samples are analysed. Thus the LTB69 pentamer migrates at approximately 90 kDa, in comparison to the expected molecular weight of 70 kDa. The periplasmic samples were also analysed by Western blotting using both anti-LTB serum and the monoclonal antibody BB05. This confirmed the identity of the fusion proteins and showed cross reactivity of the LTB69 protein with both antibodies, demonstrating that the acquisition of a foreign epitope did not destroy the antigenicity of the parental LTB molecule (data not shown).

4. Binding of fusion proteins to GM1

Figure 3A:
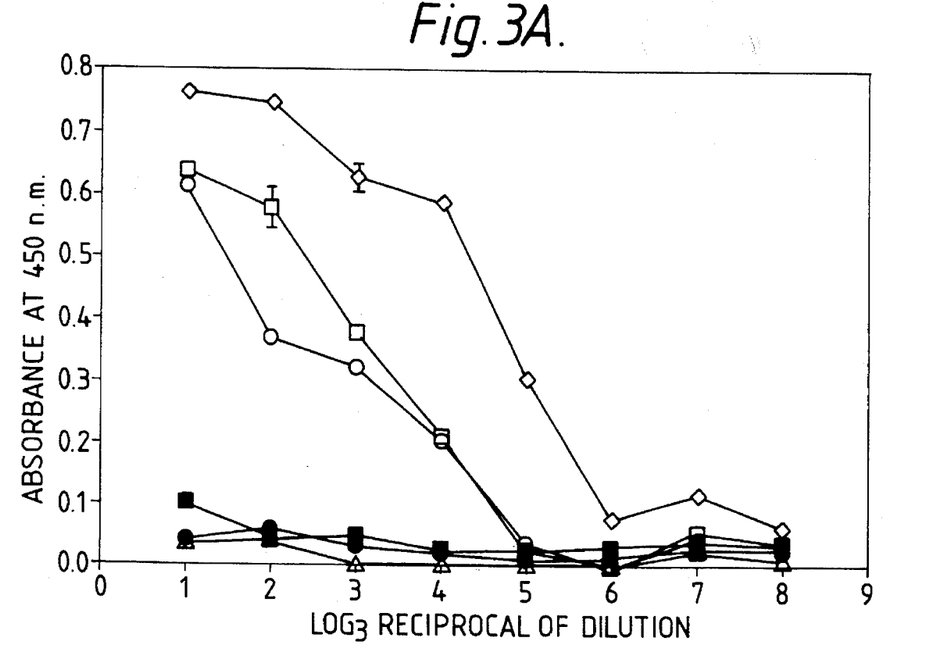
FIG. 3A and FIB. 3B show the ganglioside binding activities of periplasmic extracts from *E. coli* strains carrying plasmid pFV1 (o, ●) pFV169 (□, ■) and HB101 alone (Δ, ▲) and purified LTB (◊). The open symbols represent samples applied to GM1 coated plates and the filled in symbols represent those applied to uncoated plates. (FIG. A) plates probed with anti-LTB antibody.
Figure 3B:
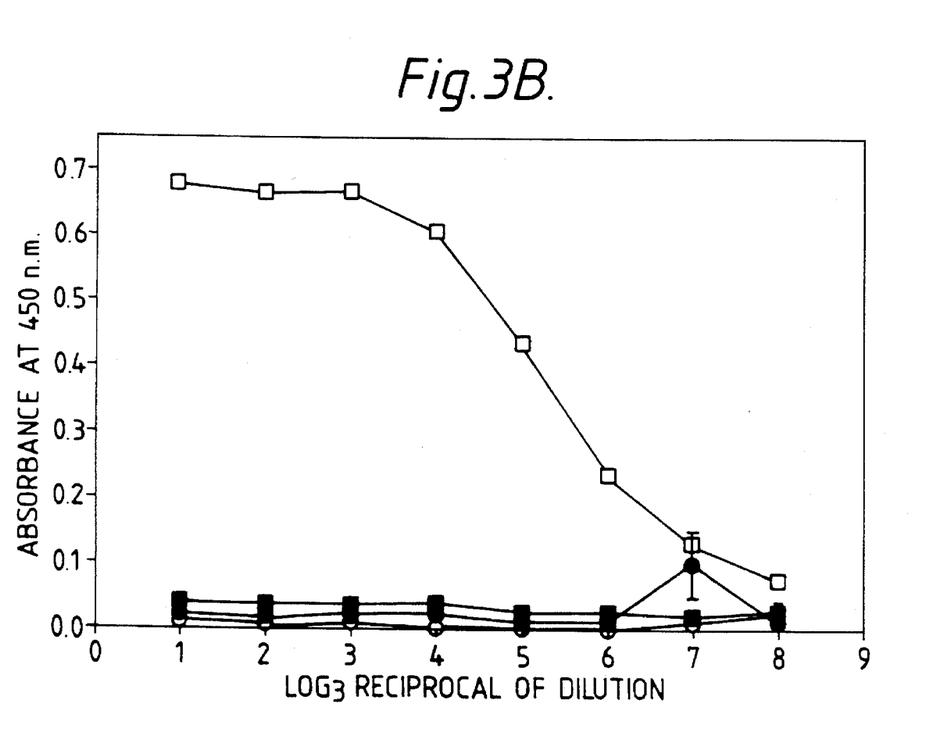

To determine if the products of pFV1 (LTBH) and pFV169 (LTB69) retained high affinity for $GM_1$ gangliosides, periplasmic fractions of *E. coli* harbouring the plasmids were analysed by a $GM_1$ ELISA using both anti-LTB serum and the monoclonal antibody BB05 as detection antibodies. The results, as shown in FIG. 3a, show that both LTBH and LTB69 bound gangliosides efficiently, and the addition of the BB05 epitope to the LTBH protein had no appreciable effect on the degree of binding of the protein to $GM_1$ gangliosides. No significant inhibition of $GM_1$ binding, relative to purified native LTB, was apparent despite the possibility of the C-terminal extensions interfering with recognition by LTB-specific antibodies. The proteins were also assayed on plates not coated with $GM_1$ gangliosides which indicated clearly the specificity of this assay (FIGS. 3a and b). When the proteins were assayed using BB05 as the detection antibody, only the LTB69 protein applied to the $GM_1$ coated plates was reactive (FIG. 3b). This demonstrates that the pentameric form of the LTB69 protein does not alter the antigenicity of the *B. pertussis* P.69 epitope carried by the molecule.

5. Partial purification of LTBH and LTB69 proteins.

Figure 4:
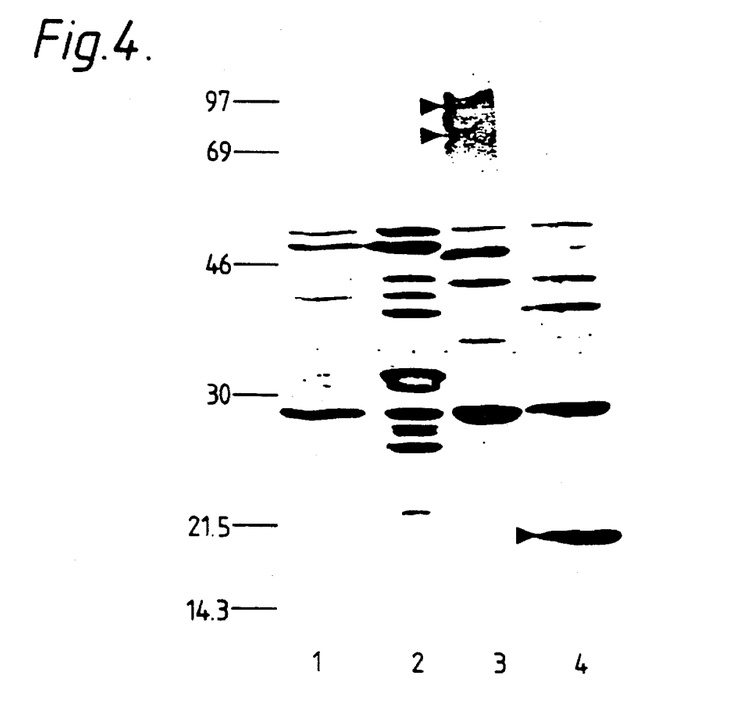

LTBH and LTB69 proteins are expressed at moderate levels, accounting for a few percent of the total protein in the periplasmic extracts (see FIG. 1). In order to study these proteins in more detail, the LTB69 fusion protein was partially purified as described in Materials and Methods. This protocol, which involved concentration of the periplasmic extract followed by DEAE Trisacryl chromatography yielded LTB69 fusion protein which was substantially purer than the starting material (see FIG. 4). Densitometry scans of such preparations of LTB69 revealed this protein to constitute between 25–30% of the total protein (data not shown).

6. Immunogenicity of the fusion proteins.

Figure 5A:
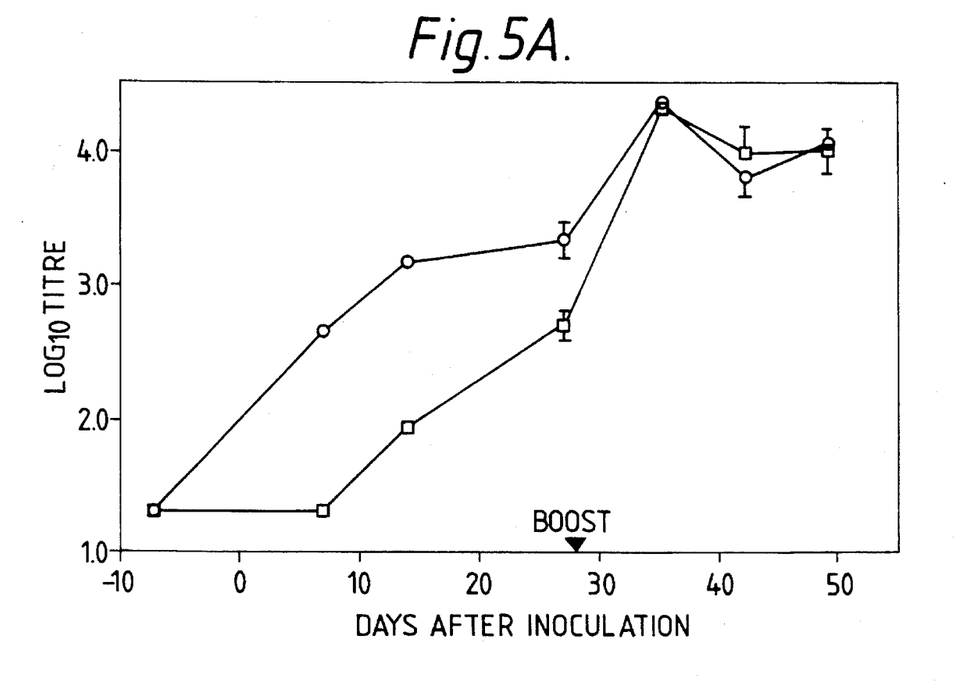
FIG. 5 shows the serum response of mice immunised intranasally with LTB or LTB69 proteins. (a) anti-LTB titres; (b) anti-P.69 titres. Mice were immunised intranasally with 20 g LTB (O) or LTB69 (□) protein and the dose repeated on day 28. Serum samples were taken during the course of the immunization and the anti-LTB and anti-P.69 titres were measured as described in Materials and Methods. (a) anti-LTB titres; (b) anti-P.69 titres.

CT, CTB and LTB have been shown to be very effective immunogens when delivered intranasally (Bessen and Fischetti, 1988, Tamura et al, 1988). We thought it interesting to investigate the immunogenicity of the purified LTB69 fusion protein when delivered intranasally to mice, particularly in light of the retention of the ganglioside binding and pentameric form of the fusion proteins. Groups of 5 mice were inoculated intranasally with 20 ug purified native LTB or LTB69, followed by a boost with the same amount of antigen 4 weeks later. Anti-LTB serum antibody was detected in groups of mice inoculated with either LTB or LTB69, although a slower primary response was detected in mice immunised with the LTB69 fusion protein. However, after boosting, the levels of antibodies in both groups increased to a similar high level (FIG. 5a).

Figure 5B:
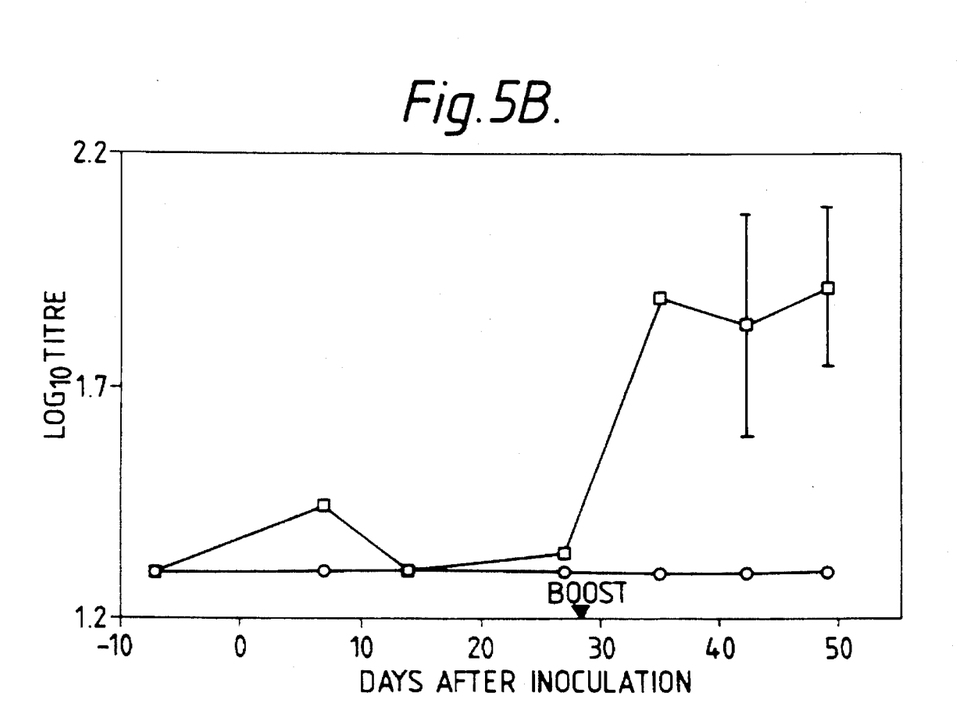

The serum response to the P.69 epitope itself showed the typical sequence of a low level primary response followed, after boosting, by a faster secondary response attaining a higher titre (see FIG. 5b). This secondary response was rather more variable than that to LTB, with some mice attaining much higher antibody levels than others.

Figure 6:
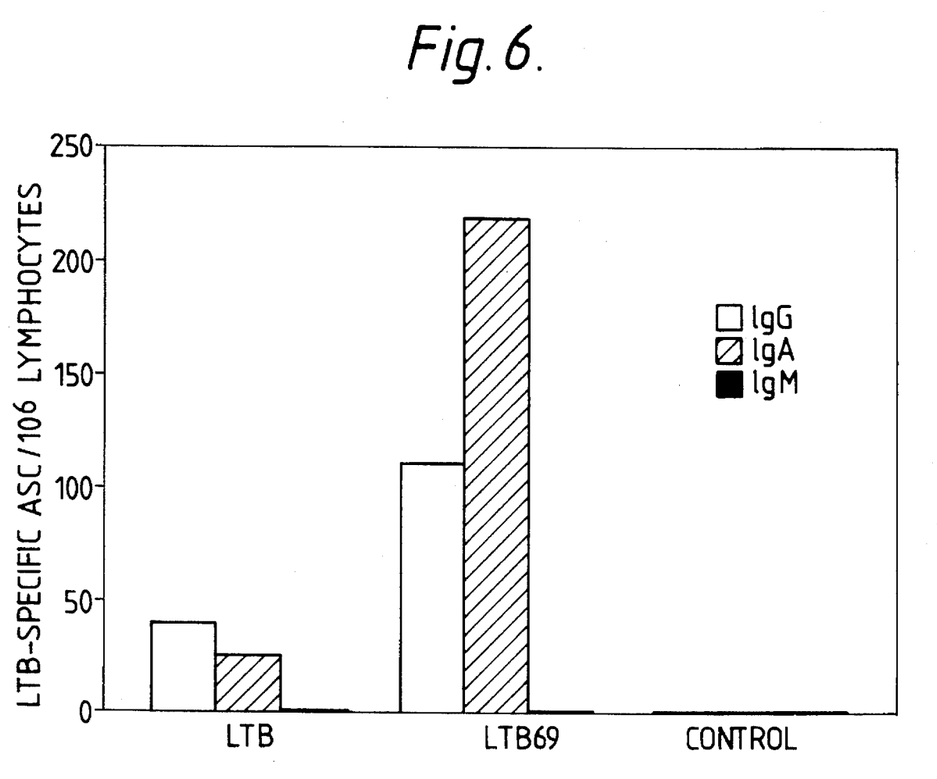
FIG. 6 shows the number of anti-LTB antibody secreting cells in the lungs of intranasally immunised mice. Mice were immunised with LTB and LTB69 proteins and lymphocytes isolated from lungs and ELISPOT assays performed to enumerate the anti-LTB secreting cells. Control ELISPOT assays performed suing medium alone are shown.

The immunised mice were also assayed for the presence of antibody secreting cells in the lungs using ELISPOT assays. Cells secreting LTB-specific IgG or IgA were found in mice immunised with LTB or LTB69 (see FIG. 6). Also, in mice immunised with LTB69, cells secreting IgG or IgM specific for P.69 could be detected. However the number of cells secreting P.69-specific antibodies was approximately 5 fold less than those secreting LTB specific antibodies (data not shown).

REFERENCES

Bessen and Fischetti (1988) *Infect. Immun.* 56: 2666–2672.
Charles et al (1986) *Nucl. Acids. Res.* 13: 4431–4443.
Clements (1990) *Infect. Immun.* 58: 1159–1166.
Clements and Finkelstein (1979) *Infect. Immun.* 24: 760–769.
Cuatrecassas (1973) *Biochemistry* 12: 3558–3566.
Czerkinsky et al (1983) *J. Immunol.* 136: 3607–3611.
Czerkinsky et al (1989) *Infect. Immun.* 57: 1072–1077.
Dallas (1983) *Infect. Immun.* 40: 647–652.
Davis et al (1980) *Advanced Bacterial Genetics: A Laboratory Manual.* Cold Spring Harbor Laboratory, Cold Spring Harbor, N. Y.
De Aizpurua and Russel-Jones (1988) *J. Exp. Med.* 167: 440–451.
Dertzbaugh and Macrina (1989) *Gene* 82: 335–343.
Dertzbaugh et al (1990) *Infect. Immun.* 58: 70–79.
Guzman-Verduzco and Kupersztoch (1987) *J. Bacteriol.* 169: 5201–5208.
Hirst et al, (1984) *J. Bacteriol.* 157: 637–642.
Jones and Ada (1990) *J. Virology* 60: 614–619.
Liang et al (1988) *J. Immunol.* 141: 1495–1501.
Maskell et al, (1987) *Microbial Path.* 2: 211–221.
Messing and Vieira (1982) *Gene* 19: 269–276.
Moss and Richardson (1978) *J. Clin. Invest.* 62: 281–285.
Novotny et al (1985) *Dev. Biol. Stand.* 61: 27–41.
Pierce (1978) *J. Exp. Med.* 148: 195–206.
Sambrook et al (1989) *Molecular Cloning, A Laboratory Manual.* Second Edition. Cold Spring Harbor Laboratory, Cold Spring Harbor, N. Y.
Sanchez et al (1988) *Gene* 64: 265–275.
Sandkvist et al (1987) *J. Bacteriol.* 169: 4570–4576.
Schodel and Will (1989) *Infect, Immun.* 57: 1347–1350.
Sharp and Li (1986) *Nucl. Acids Res.* 14: 7737–7749.
Svennerholm and Holmgren (1978) *Curr. Microbiol.* 1: 19–23.
Tabor and Richardson (1987) *Proc. Natl. Acad. Sci. (U.S.A.)* 84: 4767–4771.
Tamura et al (1988) *Vaccine* 6: 407–413.

We claim:

1. A fusion protein comprising the following elements linked in an N-terminal to C-terminal direction:
    (A) sufficient of the B subunit of cholera toxin or heat-labile enterotoxin of *Escherichia coli* such that the fusion protein forms a pentamer complex and binds to $GM_1$-ganglioside;
    (B) a hinge of from two to eight directly linked glycineproline repeats; and
    (C) a predetermined antigen or epitope of a human or animal pathogen, which antigen or epitope effects an immune response.

2. The fusion protein according to claim 1, wherein the antigen or epitope is of a respiratory- or gut-associated pathogen.

3. The fusion protein according to claim 1, wherein the antigen or epitope is of *Bordetella pertussis*.

4. The fusion protein according to claim 1, wherein the epitope is the BB05 epitope of P69 of *Bordetella pertussis*.

5. The fusion protein according to claim 1 wherein the hinge comprises two directly linked glycine-proline repeats.

6. A DNA molecule comprising the following elements encoding a fusion protein linked in a 5' to 3' direction:
    (A) a sequence encoding sufficient of the B subunit of cholera toxin or heat-labile enterotoxin of *Escherichia coli* such that the fusion protein forms a pentamer complex and binds to $GM_1$-ganglioside;
    (B) a sequence encoding a hinge of from two to eight directly linked glycine-proline repeats; and
    (C) a sequence encoding a predetermined antigen or epitope of a human or animal pathogen, which antigen or epitope effects an immune response.

7. The DNA molecule according to claim 6, wherein the antigen or epitope is of a respiratory- or gut-associated pathogen.

8. The DNA molecule according to claim 6, wherein the antigen or epitope of *Bordetella pertussis*.

9. The DNA molecule according to claim 6, wherein the epitope is the BB05 epitope of P69 of *Bordetella pertussis*.

10. The DNA molecule according to claim 6 wherein the hinge comprises two directly linked glycine-proline repeats.

11. The DNA molecule according to claim 6, wherein at least half of the codons encoding the amino acid residues of the hinge are rare codons for those residues in the host in which the fusion protein is to be expressed.

12. A vector comprising the following elements encoding a fusion protein linked in a 5' to 3' direction:
 (A) a sequence encoding sufficient of the B subunit of cholera toxin or heat-labile enterotoxin of *Escherichia coli* such that the fusion protein forms a pentamer complex and binds to $GM_1$-ganglioside;
 (B) a sequence encoding a hinge of from two to eight directly linked glycine-proline repeats; and
 (C) a sequence encoding a predetermined antigen or epitope of a human or animal pathogen, which antigen or epitope effects an immune response,
wherein the vector, in a transformed host, expresses the fusion protein.

13. The vector according to claim 12, wherein the vector is a plasmid.

14. The vector according to claim 12, wherein the antigen or epitope is of a respiratory- or gut-associated pathogen.

15. The vector according to claim 12, wherein the antigen or epitope is of *Bordetella pertussis*.

16. The vector according to claim 12, wherein the epitope is the BB05 epitope of P69 of *Bordetella pertussis*.

17. The vector according to claim 12 wherein the hinge comprises two directly linked glycine-proline repeats.

18. The vector according to claim 12, wherein at least half of the codons encoding the amino acid residues of the hinge are rare codons for those residues in the host in which the fusion protein is to be expressed.

19. A host call transformed with a vector comprising the following elements encoding a fusion protein linked in a 5' to 3' direction:
 (A) a sequence encoding sufficient of the B subunit of cholera toxin or heat-labile enterotoxin of *Escherichia coli* such that the fusion protein forms a pentamer complex and binds to $GM_1$-ganglioside;
 (B) a sequence encoding a hinge of from two to eight directly linked glycine-proline repeats; and
 (C) a sequence encoding a predetermined antigen or epitope of a human or animal pathogen, which antigen or epitope effects an immune response.

20. The host call according to claim 19, wherein said host is a strain of *Escherichia coli*.

21. The host call according to claim 19 wherein said antigen or epitope is of a respiratory- or gut-associated pathogen.

22. The host call according to claim 19 wherein said antigen or epitope is of *Bordetella pertussis*.

23. The host call according to claim 19 wherein the epitope is the BB05 epitope of P69 of *Borderella pertussis*.

24. The host call according to claim 19 wherein said hinge comprises two directly linked glycine-proline repeats.

25. The host call according to claim 19 wherein at least half of the codons encoding the amino acid residues of the hinge are rare codons for those residues in the host.

* * * * *

SEQUENCE LISTING ( 1 ) GENERAL INFORMATION:

( i i i ) NUMBER OF SEQUENCES: 11

-continued ( 2 ) INFORMATION FOR SEQ ID NO:1:

( i ) SEQUENCE CHARACTERISTICS:
        ( A ) LENGTH: 9 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:1:

```
Val Gln Gly Glu Glu Ser Asn Asp Lys
1 5
```

( 2 ) INFORMATION FOR SEQ ID NO:2:

( i ) SEQUENCE CHARACTERISTICS:
        ( A ) LENGTH: 9 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:2:

```
Lys Thr Gly Ser Gly Phe Phe Val Phe
1 5
```

( 2 ) INFORMATION FOR SEQ ID NO:3:

( i ) SEQUENCE CHARACTERISTICS:
        ( A ) LENGTH: 27 base pairs
( B ) TYPE: nucleic acid
( C ) STRANDEDNESS: single
( D ) TOPOLOGY: linear ( i i ) MOLECULE TYPE: DNA (Synthetic)

( i x ) FEATURE:
        ( A ) NAME/KEY: misc_feature
( B ) LOCATION: 1..27
( D ) OTHER INFORMATION: /function= ""hinge" between LTB protein and foreign epitope"

( x i ) SEQUENCE DESCRIPTION: SEQ ID NO:3:

CTTGGGGCCG GGGCCCGAGA TCTTTGA 27

( 2 ) INFORMATION FOR SEQ ID NO:4:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i ) MOLECULE TYPE: DNA (Synthetic)

( i v ) ANTI-SENSE: YES ( i x ) FEATURE:
( A ) NAME/KEY: misc_feature
( B ) LOCATION: 1..27
( D ) OTHER INFORMATION: /function= ""hinge" between LTB protein and foreign epitope"

( x i ) SEQUENCE DESCRIPTION: SEQ ID NO:4:

CTAGTCAAAG ATCTCGGGCC CCGGCCC 27

( 2 ) INFORMATION FOR SEQ ID NO:5:

( i ) SEQUENCE CHARACTERISTICS:
( A ) LENGTH: 75 base pairs (B) TYPE: nucleic acid
(C) STRANDEDNESS: single
(D) TOPOLOGY: linear (ii) MOLECULE TYPE: DNA (Synthetic)

(xi) SEQUENCE DESCRIPTION: SEQ ID NO:5:

GATCGCTCCG CAGCCGGGTC CGCAGCCGCC GCAGCCGCCG CAGCCGCAGC CGGAGGCGCC    60

GGCTCCGCAG CCGGA    75

(2) INFORMATION FOR SEQ ID NO:6:

(i) SEQUENCE CHARACTERISTICS:
(A) LENGTH: 75 base pairs
(B) TYPE: nucleic acid
(C) STRANDEDNESS: single
(D) TOPOLOGY: linear (iv) ANTI-SENSE: YES (xi) SEQUENCE DESCRIPTION: SEQ ID NO:6:

CTAGTCCGGC TGCGGAGCCG GCGCCTCCGG CTGCGGCTGC GGCGGCTGCG GCGGCTGCGG    60

ACCCGGCTGC GGAGC    75

(2) INFORMATION FOR SEQ ID NO:7:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:7:

Pro Gly Pro Gln Pro Pro
1               5

(2) INFORMATION FOR SEQ ID NO:8:

(i) SEQUENCE CHARACTERISTICS:
(A) LENGTH: 39 base pairs
(B) TYPE: nucleic acid
(C) STRANDEDNESS: double
(D) TOPOLOGY: linear (vii) IMMEDIATE SOURCE:
(B) CLONE: pFV1 ("hinge" region thereof)

(ix) FEATURE:
(A) NAME/KEY: CDS
(B) LOCATION: 1..39

(xi) SEQUENCE DESCRIPTION: SEQ ID NO:8:

AAA AAC TTG GGG CCG GGG CCC GAG ATC TTT GAC TAG TTT    39
Lys Asn Leu Gly Pro Gly Pro Glu Ile Phe Asp *
1               5               10

(2) INFORMATION FOR SEQ ID NO:9:

(i) SEQUENCE CHARACTERISTICS:
(A) LENGTH: 11 amino acids
(B) TYPE: amino acid
(D) TOPOLOGY: linear (ii) MOLECULE TYPE: protein (xi) SEQUENCE DESCRIPTION: SEQ ID NO:9:

Lys Asn Leu Gly Pro Gly Pro Glu Ile Phe Asp (2) INFORMATION FOR SEQ ID NO:10:

(i) SEQUENCE CHARACTERISTICS:
        (A) LENGTH: 39 base pairs
        (B) TYPE: nucleic acid
        (C) STRANDEDNESS: double
        (D) TOPOLOGY: linear     (ii) MOLECULE TYPE: DNA     (iv) ANTI-SENSE: YES     (vii) IMMEDIATE SOURCE:
        (B) CLONE: pFV1 ("hinge"region thereof)

(xi) SEQUENCE DESCRIPTION: SEQ ID NO:10:

```
AAACTAGTCA AAGATCTCGG GCCCCGGCCC CTAGTTTTT                      39
```

(2) INFORMATION FOR SEQ ID NO:11:

(i) SEQUENCE CHARACTERISTICS:
        (A) LENGTH: 33 amino acids
        (B) TYPE: amino acid
        (C) STRANDEDNESS: single
        (D) TOPOLOGY: linear     (ii) MOLECULE TYPE: peptide     (ix) FEATURE:
        (A) NAME/KEY: Region
        (B) LOCATION: 1..2
        (D) OTHER INFORMATION: /label= LTB sequence     (ix) FEATURE:
        (A) NAME/KEY: Region
        (B) LOCATION: 4..7
        (D) OTHER INFORMATION: /label= hinge region     (ix) FEATURE:
        (A) NAME/KEY: Region
        (B) LOCATION: 10..31
        (D) OTHER INFORMATION: /label= P69 BB05 epitope of Bordetella
                pertussis sequence     (xi) SEQUENCE DESCRIPTION: SEQ ID NO:11:

```
Lys Asn Leu Gly Pro Gly Pro Glu Ile Ala Pro Gln Pro Gly Pro Gln
1               5                   10                  15
Pro Pro Gln Pro Pro Gln Pro Gln Pro Glu Ala Pro Ala Pro Glu Pro
                20                  25                  30
Asp
```